United States Patent
Bajraszewski et al.

(10) Patent No.: US 9,217,707 B2
(45) Date of Patent: Dec. 22, 2015

(54) METHOD AND APPARATUS FOR EYE MOVEMENT TRACKING IN SPECTRAL OPTICAL COHERENCE TOMOGRAPHY (SD-OCT)

(75) Inventors: Tomasz Bajraszewski, Glogowo (PL); Pawel Dalasinki, Torun (PL); Jaroslaw Jaronski, Wroclaw (PL)

(73) Assignee: CANON OPTOPOL TECHNOLOGY SP. Z O.O., Wroclaw (PL)

( * ) Notice: Subject to any disclaimer, the term of this patent is extended or adjusted under 35 U.S.C. 154(b) by 359 days.

(21) Appl. No.: 13/132,388

(22) PCT Filed: Nov. 27, 2009

(86) PCT No.: PCT/EP2009/008473
§ 371 (c)(1),
(2), (4) Date: Jun. 2, 2011

(87) PCT Pub. No.: WO2010/063416
PCT Pub. Date: Jun. 10, 2010

(65) Prior Publication Data
US 2011/0235050 A1     Sep. 29, 2011

(30) Foreign Application Priority Data
Dec. 2, 2008   (EP) .................................. 08020881

(51) Int. Cl.
*G01B 11/02*  (2006.01)
*G01N 21/47*  (2006.01)
*A61B 3/113*  (2006.01)
*A61B 3/12*   (2006.01)
*G01N 21/17*  (2006.01)

(52) U.S. Cl.
CPC .......... *G01N 21/4795* (2013.01); *A61B 3/113* (2013.01); *A61B 3/12* (2013.01); *G01N 2021/1787* (2013.01)

(58) Field of Classification Search
USPC ................................................... 356/479, 497
See application file for complete search history.

(56) References Cited

U.S. PATENT DOCUMENTS

| | | | |
|---|---|---|---|
| 5,321,501 A * | 6/1994 | Swanson et al. | 356/479 |
| 7,347,548 B2 | 3/2008 | Huang et al. | |
| 7,364,296 B2 | 4/2008 | Miller et al. | |
| 7,400,410 B2 | 7/2008 | Baker et al. | |
| 7,452,077 B2 * | 11/2008 | Meyer et al. | 351/205 |
| 7,589,842 B2 * | 9/2009 | Kuroiwa | 356/497 |

(Continued)

FOREIGN PATENT DOCUMENTS

| | | | |
|---|---|---|---|
| DE | 43 09 056 B4 | 5/2006 | |
| EP | 1 882 445 | 1/2008 | |

(Continued)

OTHER PUBLICATIONS

WIPO Publication 2007084748, published Jul. 26, 2007, is the English equivalent of JP2009-523563.

(Continued)

*Primary Examiner* — Jonathan Hansen
(74) *Attorney, Agent, or Firm* — Casimir Jones, S.C.; Mary Ann Brow

(57) ABSTRACT

The invention relates to a method and an apparatus for collecting structural data with spectral optical coherence tomography from samples having a point of maximum reflectance. This point of maximum reflectance is used for adjusting the scanned path pattern.

8 Claims, 5 Drawing Sheets

(56) References Cited

U.S. PATENT DOCUMENTS 7,791,734 B2    9/2010   Olivier et al.
8,009,297 B2    8/2011   Chan et al.

FOREIGN PATENT DOCUMENTS

| JP | 2009-523563 | 6/2009 |
| WO | WO 03/070090 | 8/2003 |
| WO | 2007066465 | 6/2007 |
| WO | 2007084748 | 7/2007 |
| WO | WO 2008/052793 | 5/2008 |

OTHER PUBLICATIONS

Ferguson et al., "Tracking optical coherence tomography," Opt Lett, 29(18), p. 2139-2141 (2004).

Huang et al., "Optical coherence tomography," Science, 254, p. 1178-1181 (1991).

Szkulmowska et al., "Coherent noise-free ophthalmic imaging by spectral optical coherence tomography," J Physics D: Applied Physics, 38, p. 2606-2611 (2005).

English Translation of the Description of DE 4309056 B4, published May 24, 2006.

\* cited by examiner

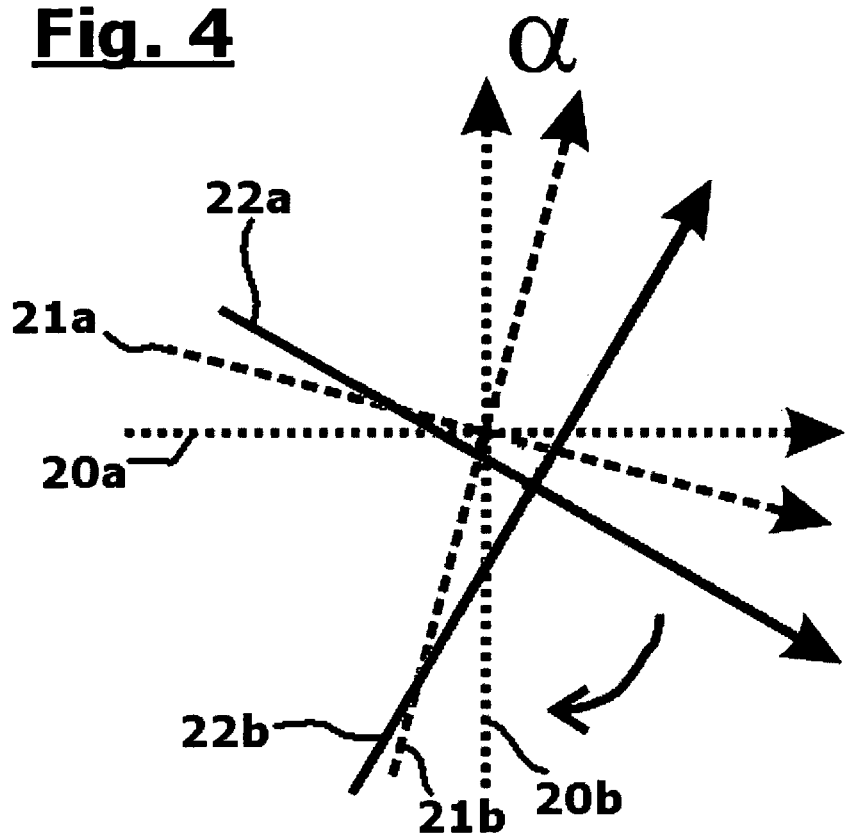

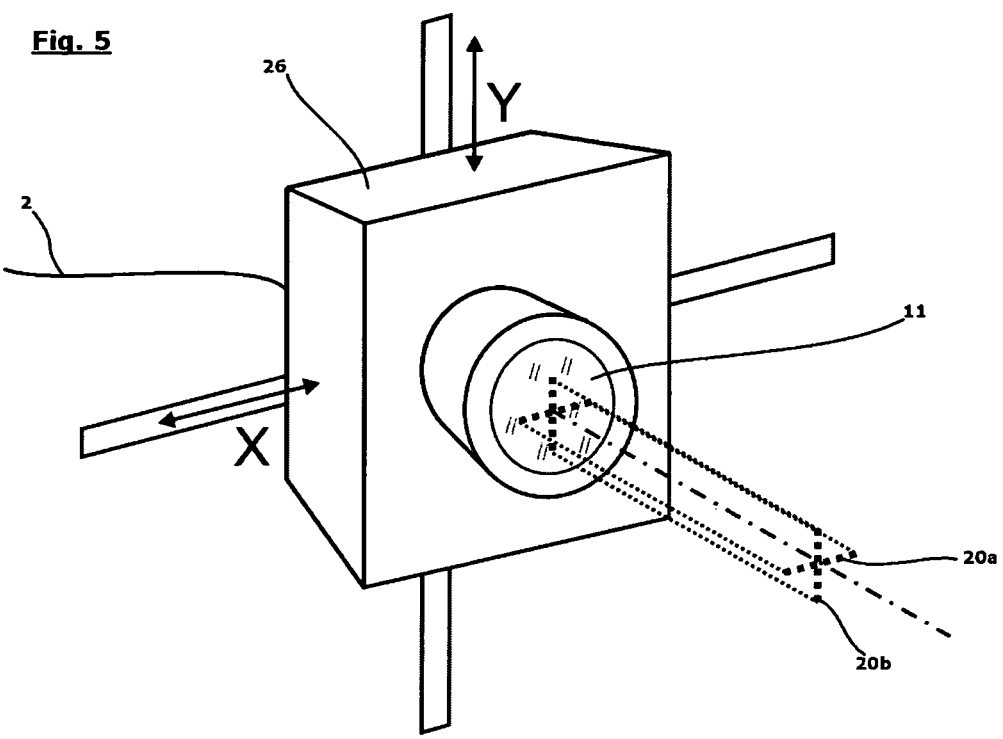

METHOD AND APPARATUS FOR EYE MOVEMENT TRACKING IN SPECTRAL OPTICAL COHERENCE TOMOGRAPHY (SD-OCT)

This application is a 371 National Entry of International Application Number PCT/EP2009/008473, filed Nov. 27, 2009, which is incorporated herein by reference in its entirety and which claims priority to European Patent Application 08020881.2, filed Dec. 2, 2008.

The invention relates to a method and an apparatus for collecting structural data with spectral optical coherence tomography from samples having a point of maximum reflectance.

Optical coherence tomography (OCT) is an interferometric technique for examination of samples consisting of partially transparent matter. According to this technique, low coherent light is divided into at least two portions. One portion is used as sample light to be passed into a sample path for illumination of the sample under investigation. The second portion is used as reference light and led through a reference path to be recombined at a point of recombination with portions of the light which are back-scattered from the sample. The recombined light contains an interferometric signal carrying information about the internal structure of the sample.

OCT was originally proposed by Huang et al., Science, Vol. 254, 1991, p. 1178 to 1181, who used a scannable optical path delay (OPD) in the reference path. The OPD is scanned in an oscillating fashion. Interference fringes occur only in positions in which the optical path length of the reference path matches the optical path length for the light back-scattered from the sample. Evaluation of these fringes and the OPD at which they occur enables identification of back-scattering structures in the sample and determination of their relative distances. Due to the time-dependence of this technique, it is generally referred to as "Time domain Optical Coherence Tomography" (TdOCT).

The invention deals with an alternative OCT modality. It is known as "Spectral Optical Coherence Tomography" (SOCT) and based upon a spectral analysis of the recombined light. The spectral data I(k) of the recombined light, i.e. the distribution of the light intensities for its spectral components, is acquired with a spectrometer ("Spectral Coherence Tomography", SOCT; see Szkulmowska et al., Journal of Physics D: Applied Physics, Vol. 38, 2005, 2606-2611). The spectral data I(k) are transformed, e.g. by way of Fourier transform or Fast Fourier Transform (FFT), to a function S(z) representing the reflectivities and relative distances of back-scattering structures within the sample (e.g. DE 43 09 056 B4).

In all OCT applications, the axis parallel to the incident light beam is usually referred to as z axis and the acquisition of data along this axis is called an "A scan". An A scan yields the data for a one-dimensional "image" from the structure inside the sample. The axes perpendicular to the z axis are referred to as x and y axis. In order to obtain two- or three-dimensional images, most OCT devices comprise scanning means which allow for scanning the light beam along one or both of these axes. A set of A scans recorded along a line perpendicular to the z axis is called a "B scan". A set of B scans taken along a plurality of lines perpendicular to the z axis provides a three-dimensional image of the sample. The invention deals with such three-dimensional imaging using SOCT.

It is not necessary that the scanning means shifts the light beam perpendicularly to the xy plane. Especially if comparatively simple pivotable mirror optics are employed for the scanning optics, the light beam may be pivoted instead of transversally shifted. In that case, the exact orientation of the z-axis is a matter of definition and the varying inclination of the incident beam may be accounted for in evaluation.

OCT has become, as a non-invasive diagnostic technique, very useful in clinical in vivo applications, especially on ophthalmology. However, its major drawback particularly in this field of use is its sensitivity to movements of the sample under investigation, especially of the human eye. Such eye movements do not pose a problem for two-dimensional imaging as two dimensional images may be generated within tens of milliseconds which is fast enough to suppress the influence of eye movements. However, three-dimensional imaging takes more time of up to a few seconds, during which eye movements occur and impair the image formation.

In order to cope with eye motion problems in retinal OCT, Ferguson et al. combined an OCT system with a hardware-based retinal tracker (OPTICS LETTERS 2004, 2139-2141). However, the additional tracking beam and steering mirrors add to the complexity of the system. Its applicability is limited to retinal OCT, because physical landmarks with suitably complex morphology are needed.

US 2008/0055543 A1 discloses a software compensation of eye motions during anterior chamber OCT. This system does not offer tracking so its correction capabilities are limited by adjustments within the image data once acquired.

The object of the invention is to suppress disturbances by movements of the sample during the data collection for three-dimensional imaging by hardware-tracking, but without the need for an extra tracking beam. The invention is applicable to samples having a point of maximum reflectance. It achieves a suppression of the disturbances by the elements of claims 1 and 7. The further claims define improvements of the invention.

The point of maximum reflectance may be any point in the plane perpendicular to the beam incident on the sample, for which the light back-scattered from the sample is reproducibly higher than for any other point in that plane. For instance, if the sample has convex or concave interfaces, the apex of such an interface may be the point of maximum reflectance. In case of examination of a human or animal eye in ophthalmology, the apex of the cornea is such a point of maximum reflectance, causing a strong corneal reflex. This effect is usually detrimental for ophthalmic application, but the invention deliberately makes use of it as a fixed point. As this fixed point moves with the sample, it can be exploited for adjustments of the scanning pattern to compensate for sample movements. The term "interface" in this respect covers surfaces of the sample as well. Likewise, the term "point" in this respect encompasses also areas which are small enough to serve as a fixed point.

The scanning lines mentioned in the main claims are preferably, but not necessarily, straight lines. The position change of step d) in claim 1 encompasses changes of orientation only or parallel shifts of the line only or combinations of both. Preferably, two scanning lines are employed as this allows the invention to work relatively fast. The scanning pattern, i.e. the particular choice of the number of scanning lines, their shape and their position change, may be chosen in dependence of the particular application. The exit condition for the method of claim 1 may be that the particular scanning pattern is accomplished.

Advantageously, the re-performing step c) of claim 1 involves that the positions of at least two of the scanning lines is changed. Such scanning patterns allow for fast measurements. In this case, it is further advantageous if the re-performing step c) involves that the angle between both scanning lines is unchanged. This causes the B scans to cover the sample in a uniform manner. In this case, it is further advantageous if the angle between both scanning lines lies in a range between 70° and 120°, more preferable between 80° and 110°, and even more preferable 90°. This renders the identification of the maxima in step b) of claim 1 relatively simple. Especially if the two scanning lines are straight lines, they have an almost or exact Cartesian shape and serve as coordinates so that the calculation of the adjustment in step d) of claim 1 can be kept very simple saving computation time.

Apart from that, it is advantageous if identifying the maxima of light intensity according to the identification step b) of claim 1 involves splitting the light returning from the sample into a first portion used for spectral optical coherence tomography and a second portion used for detecting the light intensity. Using a portion of the light separate from the portion used for spectral analysis in the SOCT evaluation increases speed and sensitivity of the invention. Common SOCT devices employ typically CCD arrays for the measurement of the intensities of the spectral components during spectral analysis. Determining the overall light intensity from the signal generated by such a sensor is rather cumbersome and slow. Using a separate portion of the light for step b) allows to perform the invention without any reduction of the speed of the SOCT measurement. For these reasons, an apparatus according to the invention advantageously comprises a light intensity detector arranged for measuring the intensity of the light returning from the sample and for transmitting a signal representing the light intensity to said scan controlling means.

In the latter case, it is further advantageous if said light intensity detector is arranged for measuring the intensity of the light recombined by said means for recombining light exiting from the sample path and light exiting from the reference path. Using the recombined light for the intensity measurement is advantageous as in that case the invention has no impact on the sensitivity of the SOCT measurement. It is in this case further advantageous if said means for recombining light exiting from the sample path and light exiting from the reference path is an optical coupler, a first port of which is connected to said spectral analysis means and a second port of which is connected to said light intensity detector. This renders the design of the apparatus of the invention simple and, as optical couplers are used as recombination means anyway, reduces the number of optical components.

Apart from that, it is advantageous if the apparatus according to the invention further comprises a holder on which said scanning means is mounted and driving means arranged for translating said holder perpendicularly to the probing beam. These elements facilitate compensation of sample movements which are too large to be compensated by adjusting offsets in the scanning means. In this case, it is further advantageous if said driving means is arranged for translating said holder in two dimensions perpendicularly to the probing beam so compensations in all directions are possible. It is further advantageous if said scan controlling means is configured to change the positions of scanning lines by adjusting offsets in the scanning means in case of small offsets determined in step c) and by translating said holder in case of larger offsets determined in step c). In that case the apparatus may choose the preferable mode of compensation so that the operation is optimized. Fine displacements are compensated for within the scanning means, while larger adjustments are made by translating the entire scanning means.

A light source may be any source of electro-magnetic radiation in the range between 600 nm to 1,700 nm with sufficient coherence characteristics for SOCT, e.g. superluminescent diodes. The terms "light", "optical" and "optics" within the meaning of the invention denote that the respective elements or steps influence or are influenced by such radiation. For instance, a "light intensity detector" is a detector measuring light intensities of radiation within the aforementioned range. The characteristics of such a light intensity detector may be adapted to the sample under investigation. For instance, if the point of maximum reflectivity may be detected without ambiguities in a small spectral range, the light intensity detector should be sensitive especially in this range, while the sensitivity for other wavelengths may be low or even zero.

An exemplary embodiment of the invention will now be described in greater detail with the help of drawings, in which FIG. 1 is a schematic block diagram showing an apparatus according to the invention;

FIG. 4 illustrates a scan pattern according to the invention where a movement of the sample has occurred;

FIG. 5 is a perspective view of translatable scanning means of an apparatus according to the invention.

Figure 1:
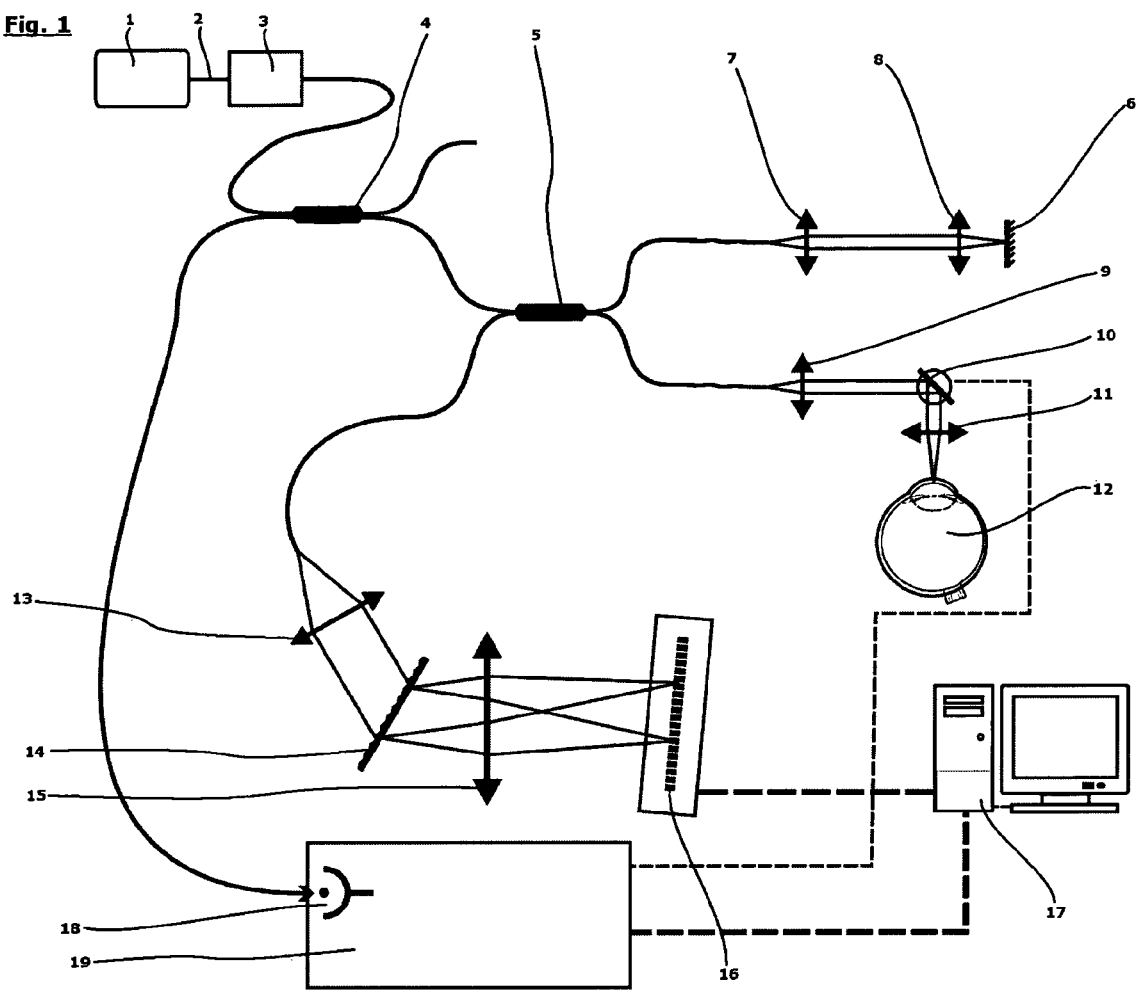

A light source 1 emits light into an optical fiber system 2. The light passes an optical isolator 3 which prevents returning light from damaging the light source 1. The light then reaches a first optical coupler 4, the function of which will become apparent when the processing of the returning light is discussed. The light propagates along one of the opposite ports of the first optical coupler 4 to second optical coupler 5 acting as beam splitter for a fiber optics Michelson interferometer. The reference path of this interferometer extends from one port of the second optical coupler 5 along a termination of the optical fiber system 2 from where it is collimated and focused on a reference mirror 6 by lenses 6 and 7. The sample path extends from another port of the second optical coupler 5 along a termination of the optical fiber system 2 and scanning means to a sample 12, which is a human eye in this example. Said scanning means comprises a collimating lens 9, mirror optics 10 and a focusing lens 11. The mirror optics 10 can be a single, two or multiple mirror system allowing to shift the light beam in two dimensions perpendicular to its axis. One mirror is illustrated in FIG. 1 for simplicity.

The light portions travelling through the reference path and the sample path return to the second optical coupler 5, in which they are recombined. One portion of the recombined light exits one port of the second optical coupler 5 and propagates to a termination of the optical fiber system 2. The light exiting the optical fiber system 2 at this termination is collimated by a collimating lens 13 and directed to a grating 14, where the light is spectrally decomposed. The spectrally decomposed light portions are focused by a focusing lens 15 on a pixel sensor array 16 for measurement of the light intensities of the spectrally decomposed light portions. The pixel sensor array 16 converts the intensities into an electric signal which is transmitted to a computer 17 for numerical calculation of the relative positions of back-scattering interfaces along the probing beam incident on the sample 12 (A scan).

Another portion of the light recombined by the second optical coupler 5 exits another port of this coupler 5 to return to the first optical coupler 4. From here, one portion exits the port which is not connected to the light source 1, but to an intensity detector 18 for measuring the light intensity without spectral decomposition. The light portion passing through the other port of said first optical coupler 4, which port is connected to the light source 1, is prevented from entering the light source by optical isolator 3.

In this example, the intensity detector 18 is part of a hardware scan controlling means 19 communicating electronically with the scanning means. The intensity detector 18 may alternatively be connected to the computer 17 equipped with software performing the same function as the hardware scan controlling means 19.

Figure 2:
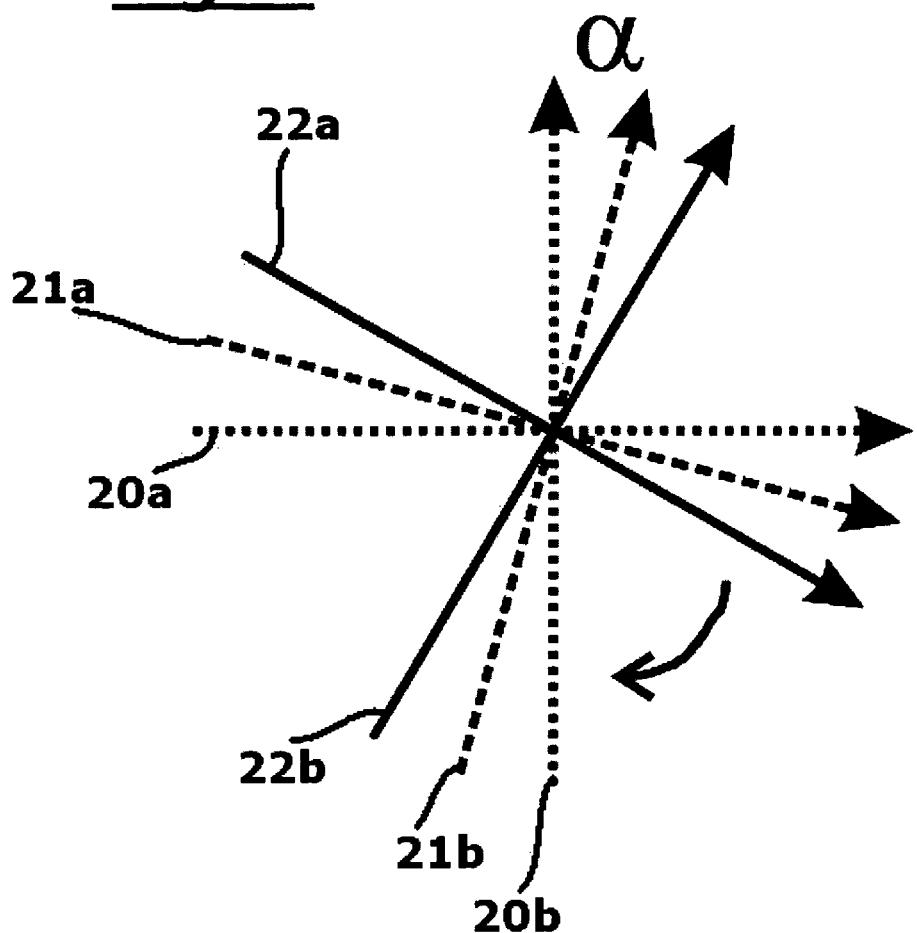
FIG. 2 illustrates a scan pattern according to the invention where no movement of the sample occurs.

The scan controlling means 19 controls the mirror optics 10 of the scanning means so that the probing beam incident on the sample 12 follows a scan pattern determined by the scan controlling means 19 (B scans). If no movement of the sample 12 occurs during the collection of the data, the scan pattern in this example is that of FIG. 2. First, two B scans are performed along the two perpendicular dotted scanning lines 20a, 20b. The scan directions are represented by arrows but may be chosen arbitrarily. The intersection of the dotted scanning lines 20a, 20b may advantageously be located by the operator at the point of maximum reflectance of the sample 12. After completion of these first two B scans, the second two B scans are performed along the two perpendicular dashed scanning lines 21a, 21b which are inclined by an angle α with respect to the first scanning lines 20a, 20b, but share the same point of intersection. Similarly, the third two B scans are performed along the solid scanning lines 22a, 22b which are inclined to the former scanning lines 21a, 21b by the same angle α. In the absence of any movement of the sample 12, this scan pattern may be completed by further B scans in an analogous manner until the B scans have covered the entire surface of interest of the sample 12.

Figure 3:
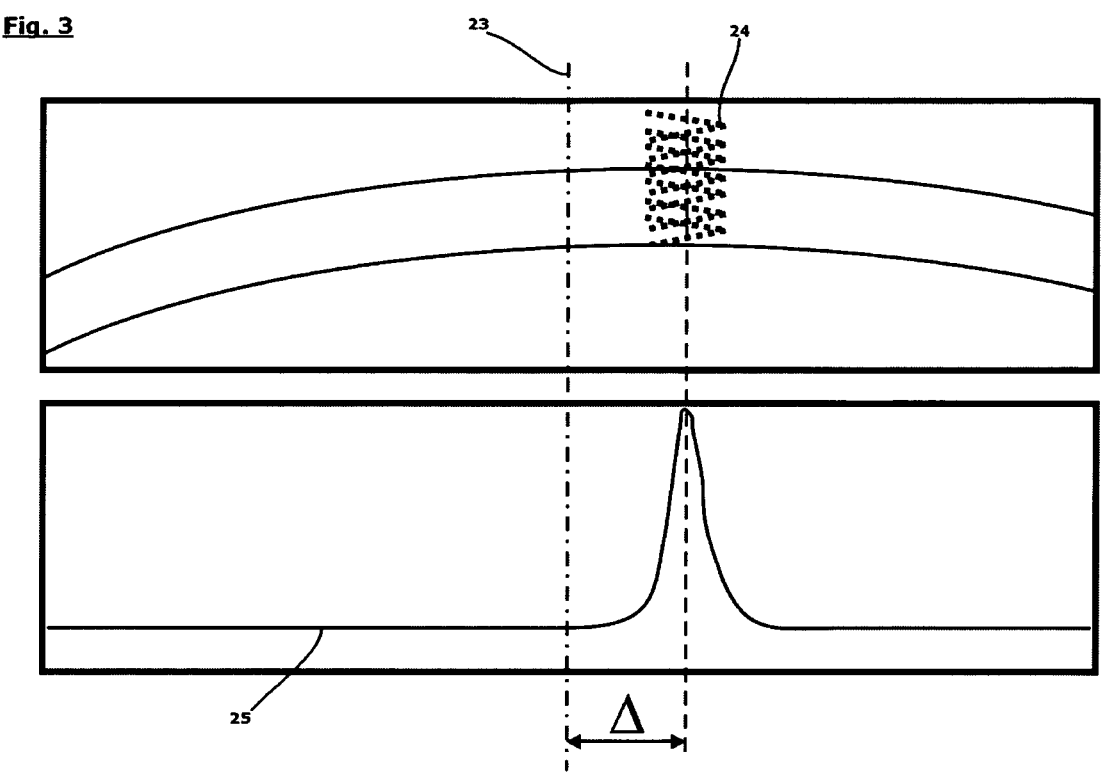
FIG. 3 is, in its upper part, an elevational view of a sample with spherical interfaces in which a strong central reflection which is displaced from the intersection of the scanning lines and shows, in its lower part, the intensity distribution of back-scattered light.

If, however, a movement of the sample 12 occurs during the measurement, the situation will be that shown in FIG. 3. The dotdashed line 23 represents the point of intersection of two consecutive B scans with linearly independent intersecting scanning lines. The accumulation 24 of dots represents the strong central corneal reflex which may be the point of maximum reflexion if, as in the example, the sample 12 is a human eye. The movement of the sample 12 causes a displacement Δ of this point of maximum reflexion from the point of intersection. This displacement must be compensated for the next B scans in order to maintain the correct spatial relationship between the B scans.

In order to accomplish such a compensation, the light intensity of the light returning from the sample is measured for each A scan with said intensity detector 18. The solid line 25 in FIG. 3 represents these intensity values taken along a scanning line. The central corneal reflex causes a sharp increase of the intensity the position of which, and thus the displacement Δ, is registered by scan controlling means 19. If the displacement Δ for at least one scanning line is other than zero, the scan controlling means 19 causes the scanning means to shift the point of intersection of the scanning lines for the following B scans, as illustrated in FIG. 4. The B scans for which a displacement Δ≠0 has been detected may be discarded and re-performed without changing the angle α, or simply discarded, or the displacement may be accounted for in the further numerical evaluation, as preferred in the particular application.

Small displacements Δ may be compensated by simply adjusting offsets of the angles in the mirror optics 10. If a displacement is too large to be compensated by the offsets of the angles in the mirror optics 10, it can nevertheless be compensated by translating the entire scanning means, as illustrated in FIG. 5. The fiber optics system 2 of the sample path is connected to a casing 26 which encloses the lenses 9 and 11 as well as the mirror optics 10. The entire casing may be translated in two perpendicular directions symbolized by arrows X and Y. In this way, the scanning lines 20a, 20b may be shifted along large distances to compensate for large displacements. The driving means (not shown) for the translations may be linear motors or other means as will be appreciated by the person skilled in the art.

The invention claimed is:

1. Method for collecting structural data with spectral optical coherence tomography from samples (12) having a point of maximum reflectance comprising the steps of
   a) performing a set of at least two B scans along at least two scanning lines (20a, 20b, 21a, 21b, 22a, 22b) which scanning lines (20a, 20b, 21a, 21b, 22a, 22b) are linearly independent and intersecting at a point of intersection;
   b) identifying the maxima of light intensity along said scanning lines (20a, 20b, 21a, 21b, 22a, 22b);
   c) determining the offset of said maxima from said point of intersection;
   d) re-performing steps a) to c), whereby the position of at least one of said scanning lines (20a, 20b, 21a, 21b, 22a, 22b) is changed and the point of intersection is adjusted in dependence of the result of the determination step c).

2. Method for collecting structural data according to claim 1, characterized in that the re-performing step c) involves that the positions of at least two of the scanning lines (20a, 20b, 21a, 21b, 22a, 22b) is changed.

3. Method for collecting structural data according to claim 2, characterized in that the re-performing step c) further involves that the angle between both scanning lines (20a, 20b, 21a, 21b, 22a, 22b) is unchanged.

4. Method for collecting structural data according to claim 3, characterized in that the angle between both scanning lines (20a, 20b, 21a, 21b, 22a, 22b) lies in a range between 70° and 120°.

5. Method for collecting structural data according to claim 4, characterized in that the angle between both scanning lines (20a, 20b, 21a, 21b, 22a, 22b) is 90°.

6. Method for collecting structural data according to claim 1, characterized in that identifying the maxima of light intensity according to the identification step b) involves splitting the light returning from the sample (12) into a first portion used for spectral optical coherence tomography and a second portion used for detecting the light intensity.

7. Method for collecting structural data according to claim 3, characterized in that the angle between both scanning lines (20a, 20b, 21a, 21b, 22a, 22b) lies in a range between 80° and 110°.

8. Method for collecting structural data according to claim 1, wherein the position of at least one of said scanning lines (20a, 20b, 21a, 21b, 22a, 22b) is changed and the point of intersection is adjusted in dependence on the result of the determining in step c) by adjusting offsets in a scanning means (10), in the case of small offsets determined in step c), or by translating a holder (26) on which said scanning means (10) is mounted, in the case of larger offsets determined in step c).

* * * * *